(12) United States Patent
Cho et al.

(10) Patent No.: US 10,034,727 B2
(45) Date of Patent: Jul. 31, 2018

(54) ARTICULATOR

(71) Applicants: Young Sun Cho, Seoul (KR); Rafael Wonjun Choi, Clarksburg, MD (US)

(72) Inventors: Young Sun Cho, Seoul (KR); Rafael Wonjun Choi, Clarksburg, MD (US)

(*) Notice: Subject to any disclaimer, the term of this patent is extended or adjusted under 35 U.S.C. 154(b) by 0 days.

(21) Appl. No.: 15/280,182

(22) Filed: Sep. 29, 2016

(65) Prior Publication Data

US 2017/0095318 A1    Apr. 6, 2017

(30) Foreign Application Priority Data

Oct. 2, 2015 (KR) .................. 10-2015-0138962

(51) Int. Cl.
*A61C 11/06* (2006.01)
*A61C 11/02* (2006.01)

(52) U.S. Cl.
CPC ............. *A61C 11/06* (2013.01); *A61C 11/02* (2013.01)

(58) Field of Classification Search
CPC ......... A61C 11/06; A61C 11/02; A61C 9/002; A61C 1/084
See application file for complete search history.

(56) References Cited

U.S. PATENT DOCUMENTS

| | | | | |
|---|---|---|---|---|
| 4,184,255 A * | 1/1980 | Gordon | ........... | A61C 7/08 433/49 |
| 4,305,708 A * | 12/1981 | Beu | ........... | A61C 11/022 433/57 |
| 4,496,319 A * | 1/1985 | Steinbock | ........... | A61C 11/022 433/56 |
| 4,981,437 A * | 1/1991 | Wilcox | ........... | A61C 11/022 433/55 |
| 5,366,373 A * | 11/1994 | Mumolo | ........... | A61C 11/022 433/58 |
| 6,019,601 A * | 2/2000 | Cho | ........... | A61C 9/002 433/34 |
| 6,247,927 B1 * | 6/2001 | Walter | ........... | A61C 9/002 433/54 |
| 6,318,999 B1 * | 11/2001 | Kim | ........... | A61C 9/002 433/60 |
| 6,402,513 B1 * | 6/2002 | Sim | ........... | A61C 9/002 433/34 |
| 2004/0131990 A1 * | 7/2004 | Doviack | ........... | A61C 11/02 433/60 |
| 2004/0197729 A1 * | 10/2004 | Honstein | ........... | A61C 9/002 433/34 |

(Continued)

*Primary Examiner* — Nicholas Lucchesi
(74) *Attorney, Agent, or Firm* — Ichthus International Law PLLC

(57) ABSTRACT

An articulator for dental use includes a first base, a second base coupled to the first base, and an occlusion pin configured to couple the first base and the second base in a closed position. The first base includes a first base body including a first groove configured to receive plaster, a first hinge portion configured to extend outwardly from one end of the first base body, and a plurality of pin holes. The second base includes a second base body including a second groove configured to receive the plaster, a second hinge portion configured to extend outwardly from one end of the second base body, and a plurality of guide pin holes. The second hinge portion is configured to couple to the first hinge portion via the occlusion pin in the closed position.

14 Claims, 12 Drawing Sheets

(56) References Cited

U.S. PATENT DOCUMENTS

| | | | |
|---|---|---|---|
| 2006/0204920 A1* | 9/2006 | Costello | A61C 11/02 433/57 |
| 2007/0231770 A1* | 10/2007 | Huffman | A61C 9/002 433/60 |
| 2008/0138769 A1* | 6/2008 | Lim | A61C 9/002 433/213 |
| 2013/0149661 A1* | 6/2013 | Yoo | A61C 11/025 433/57 |
| 2013/0288193 A1* | 10/2013 | Gallacher | A61C 11/02 433/57 |
| 2014/0080088 A1* | 3/2014 | Kim | A61C 11/08 433/57 |
| 2016/0220336 A1* | 8/2016 | Byun | A61C 11/06 |

\* cited by examiner

ARTICULATOR

CROSS-REFERENCE TO RELATED APPLLICATION(S)

This application is based upon and claims the benefit of priority of a prior Korean Patent Application No. 10-2015-0138962, titled "Articulator," filed on Oct. 2, 2015, the content of which is incorporated herein by reference in its entirety.

TECHNICAL FIELD

The present invention relates to a device for use in dental restorations, in particular, to an articulator that provides a more accurate and convenient way to create a prosthesis on a tooth model.

BACKGROUND

There are three parts that make up a dental implant: a crown or cap, a dental abutment, and an implant. The dental abutment is attached to the implant so that the crown or cap can be placed on the dental abutment to provide a dental patient with new teeth. People who have an implant and abutment may have repaired teeth replacing natural teeth they had.

In general, in dentistry, through temporomandibular joint (TMJ) movements, an over-all structure of teeth may be in an oval shaped arc so that one can chew food through occlusion of upper and lower teeth. The word "occlusion" refers to a relationship between the upper and lower teeth, e.g., the alignment of teeth and the way the upper (maxillary) and lower (mandibular) teeth fit together in a bite. That is, dental occlusion may be described as contact between the teeth of the upper and lower jaw of a person. In the full bite, high rounded parts on a tooth surface of a tooth may come in contact with a grove of an opposing arch teeth in the maximum full bite.

As such, if the occlusion is not obtained, certain problems may occur with the occlusion, resulting in teeth damage which may bring forth teeth dysfunction. In this case, a dental device or a dental prosthetic crown may be used for repair. That is, the dental prosthetic device or crown may be made and placed on to a damaged tooth in order to repair the damaged tooth. In the description herein, a dental crown may include a tooth shaped cap that is placed over a tooth to cover the tooth to restore its shape and size, strength, and improve its appearance. Crowns are used most commonly to entirely cover or cap a damaged tooth or cover an implant.

For accurate manufacture and mounting of a dental crown, an existing or conventional technology may require a variety of devices including an oral impression, a model assembly and an articulator. In the conventional technology or method, an impression of a person's teeth and oral structure is first taken and made, and then the impression may be attached to an articulator assembly to determine an exact shape (or size) and location of an tooth for which an artificial tooth is to be produced or manufactured. Plaster may then be applied onto the impression and may be hardened or cured for a certain period of time. After the hardening process, it is reattached to the articulator assembly for further procedures. This conventional technique may involve a very complicated procedure and take a long time because of use of the plaster.

Typically, an existing model assembly comprises a mounting plate and a body to which the mounting plate is coupled. An oral model may be mounted on the mounting plate which will be cut into a unit tooth at a location of a target tooth for which it is to be manufactured.

However, there are many problems with the existing model assembly as described herein. Some of the existing technology as well as problems are described in a Korean Patent Application No. 10-20120140593. For example, when plaster is applied in a coupling portion of the mounting plate and the body of the model assembly, it may take a long time for curing to be completed due to use of the plaster, and it may produce an excessive amount of dust and sludge. Also, when the mounting plate is cut, shaking or movement may result adding to inaccuracy as a result. Further, when separating the mounting plate that is cut from the body of the model assembly, there may be some inconvenience of using a hammer to give a certain amount of impact on a pin on the mounting plate to remove and separate a prosthetic tooth. As a result, the forming an accurate contact area between teeth may be difficult.

Further, with the existing model assembly, there may be a certain amount of accuracy error arising out of or in connection with a conventional cutting process, in which an operator or technician may have to rely on their past experiences of locating places for the cutting. Thus, in the conventional cutting process, a lower pin of the mounting plate may be damaged or even cut by accident.

Further, as noted above, in the existing technique or method, the plaster is first applied to a dental impression of a patient, and then the plaster is hardened or cured. After the hardening process, an artificial tooth may be separated and reattached to an articulator for additional work by the operator or technician. This is a complicated procedure and may take a long time, in particular, due to the use of the plaster in the process. Furthermore, in the existing technique or method, positioning of a pin at a center of a tooth or abutment may be difficult, and an excessive application of the plaster to the articulator may cause it to overflow causing more problems.

As such, there is a need for further improved technology including an improved articulator that will enable manufacture of a dental restoration in a more convenient, faster, and accurate manner and for the method and techniques thereof.

SUMMARY

The present disclosure provides an exemplary embodiment of an articulator for dental use which enables more convenient, faster, and accurate manufacture of a dental restoration or prosthesis. In the articulator disclosed herein, one or more position pins are used for the easy, faster, and accurate manufacture of the dental restoration or prosthesis, and one or more guide pins may be used to guide the operator or technician to a center location of an abutment for the dental restoration in a more accurate manner, thereby enabling the operator or technician to perform an accurate occlusion task on the abutment.

The articulator disclosed herein comprises a first base, a second base coupled to the first base, and an occlusion pin. The first base includes a first base body comprising a first groove configured to receive gypsum, a first hinge portion coupled to the first base body and configured to extend outwardly from one end of the first groove, and a plurality of pin holes coupled to the first base body. The second base includes a second base body comprising a second groove configured to receive the gypsum, a second hinge portion coupled to the second base body and configured to extend outwardly from one end of the second groove, and a plurality of guide pin holes disposed in the second groove, the second hinge portion being configured to couple to the first hinge portion of the first base. The occlusion pin is configured to couple the first base and the second base.

In an aspect of the present disclosure, the first hinge portion of the first base may comprise a pair of extension couplers disposed on a first extension part coupled to one end of the first base body. The pair of extension couplers of the first hinge portion is configured to include a left first extension coupler and a right first extension coupler.

In another aspect of the present disclosure, the second hinge portion of the second base may comprise a pair of extension couplers disposed on a second extension part coupled to one end of the second base body. The pair of extension couplers of the second hinge portion is configured to include a left second extension coupler and a right second extension coupler. Further, the left first extension coupler of the first hinge portion may couple to the left second extension coupler of the second hinge portion, and the right first extension coupler of the first hinge portion may couple to the right second extension coupler of the second hinge portion.

In another aspect of the present disclosure, the left first extension coupler of the first hinge portion may comprise a first stopper, a first coupler, and an extension body, and the right first extension coupler of the first hinge portion comprises a first coupling groove and an extension body. Also, the left second extension coupler of the second hinge portion comprises a second coupling groove and an extension body, and the right second extension coupler of the second hinge portion comprises a second stopper, a second coupler, and an extension body.

In another aspect of the present disclosure, the first groove of the first base may comprise a plurality of protrusions on a bottom surface of the first groove.

Still in another aspect of the present disclosure, the first base may comprise a plurality of overflow prevention walls surrounding the first groove to prevent overflows of gypsum or plaster when applied. Further, the first base may further comprise a plurality of interlocking parts configured to receive an occlusion pin. Also, the first base may further comprise one or more guide pin markers on a side wall of the first groove. The one or more guide pin markers are configured in such a way that the operator or technician may use the one or more guide pin markers to cut and separate individual tooth being manufactured on the articulator.

Further, in an aspect of the present disclosure, the second groove of the second base may include a plurality of guide pin holes configured to accommodate a plurality of guide pins.

Still further, in another aspect of the present disclosure, the second base may include one or more guide pin markers on a side wall of the second groove, which will be in alignment with the one or more guide pin markers on the side wall of the first grove when the first base and the second base are folded together in a closed position or for an occlusion operation.

In aspect of the present disclosure, the second base may include a plurality of overflow prevention walls surrounding the second groove to prevent overflows of the gypsum or plaster being applied to the second base. The second base may further include a plurality of interlocking parts configured to receive the occlusion pin, and the plurality of interlocking parts of the second base corresponds to the plurality of interlocking parts of the first base, when the first base and the second base are folded together in the closed position or for the occlusion operation. Also, the second groove of the second base may include a plurality of protrusions disposed on a bottom surface of the second groove and configured to ensure cohesion of the gypsum or plaster when the gypsum or plaster is applied.

In an aspect of the present disclosure, the plurality of protrusions may be disposed on the bottom surface of the second groove in a symmetric pattern around the plurality of guide pin holes.

In an aspect of the present disclosure, the occlusion pin may comprise a handle portion, an elongated body coupled to the handle, and a protrusion extension point at one end of the elongated body, the protrusion extension point having an angle with respect to a center line of the elongated body. Further, the protrusion extension point may include a predetermined angle of about 20 to 30 degrees with respect to the center line of the elongated body. Furthermore, the occlusion pin may include one or more occlusion guide channels in a longitudinal direction along an elongated body of the occlusion pin, and the one or more occlusion guide channels may be configured to correspond to interlocking parts of the first base or the second base. That is, the one or more occlusion guide channels are configured to mate with protrusions in the interlocking parts of the first base or the second base.

In an aspect, the present technology may include one or more position pins which may enable and facilitate fast and accurate manufacture of prosthesis. That is, through the one or more position pins, more accurate guidance may be provided, through the one or more position pins, to a center position of a prosthetic abutment to be formed on an impression body, thereby improving accuracy.

In another aspect, the position of the prosthetic abutment may be adjusted on the oral impression disposed on the first base, increasing the accuracy for manufacturing the prosthetic abutment with one or more guide pins, and reducing a chance of having any unnecessary operation by the technician. Further, the present disclosure may be easily performed for a front occlusal bite of the prosthetic abutment. As such, in various aspects of the present technology, the accuracy and workability on the articulator may be improved greatly.

These and other features of the present disclosure will become more fully apparent from the following description and appended claims.

BRIEF DESCRIPTION OF THE DRAWINGS

A more detailed understanding may be obtained from the following description in conjunction with the accompanying drawings.

DETAILED DESCRIPTION

Figure 1:
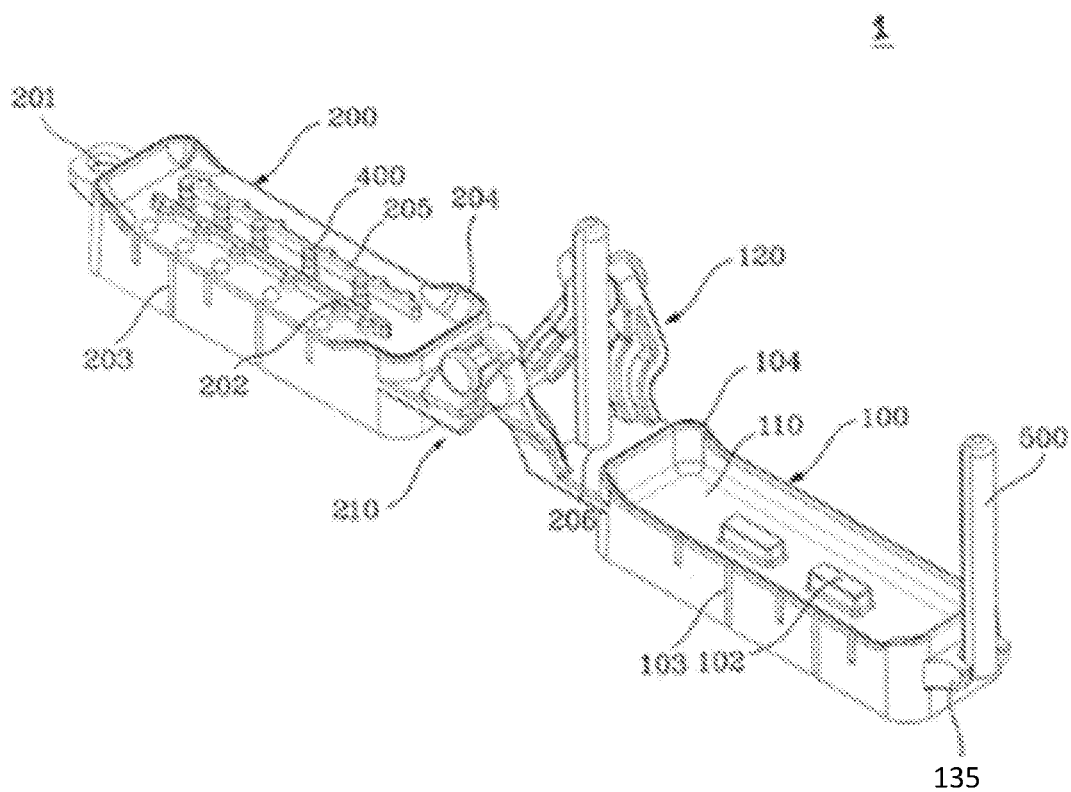
FIG. 1 is a diagram conceptually illustrating an example of an embodiment in accordance with an aspect of the present disclosure.

The detailed description of illustrative examples will now be set forth below in connection with the various drawings. The description below is intended to be exemplary only and in no way limit the scope of the claimed invention. For example, it is intended to provide a detailed example of possible implementation(s), and is not intended to represent the only configuration in which the concepts described herein may be practiced. As such, the detailed description includes specific details for the purpose of providing a thorough understanding of various concepts, and it is noted that these concepts may be practiced without these specific details. In some instances, well known structures and components are shown in block diagram form in order to avoid obscuring such concepts. It is also noted that like reference numerals are used in the drawings to denote like elements and features.

While for the purpose of simplicity the methodologies or aspects may be described herein as a series of steps or acts, it is to be understood that the claimed subject matter is not limited by the order of steps or acts, as some steps or acts may occur in different orders and/or concurrently with other acts from that shown and described herein. Further, not all illustrated steps or acts may be required to implement various methodologies or aspects according to the present disclosure disclosed herein.

FIG. 1 shows an example diagram of an articulator in an open configuration, in accordance with an aspect of the present disclosure. In the example shown in FIG. 1, an articulator 1 may include a first base 100 (or interchangeably referred to herein as the "lower base") and a second base 200 (or interchangeably referred to herein as the "upper base"), and the second base 200 is coupled to the first base 100 via a first hinge portion 120 and a second hinge portion 210.

Alternatively, the first base 100 and the second base 200 may be in a closed configuration as shown in FIG. 4, as an articulator in an occlusion position, through the operation of the first hinge portion 120 and the second hinge portion 210. The first hinge portion 120 and the second hinge portion 210 are configured to put the articulator in either an open configuration or a closed configuration for various operations. Further, in the present disclosure, the closed configuration may be referred to as a "folded mode or configuration" or an "occlusion position" of the articulator.

Figure 2:
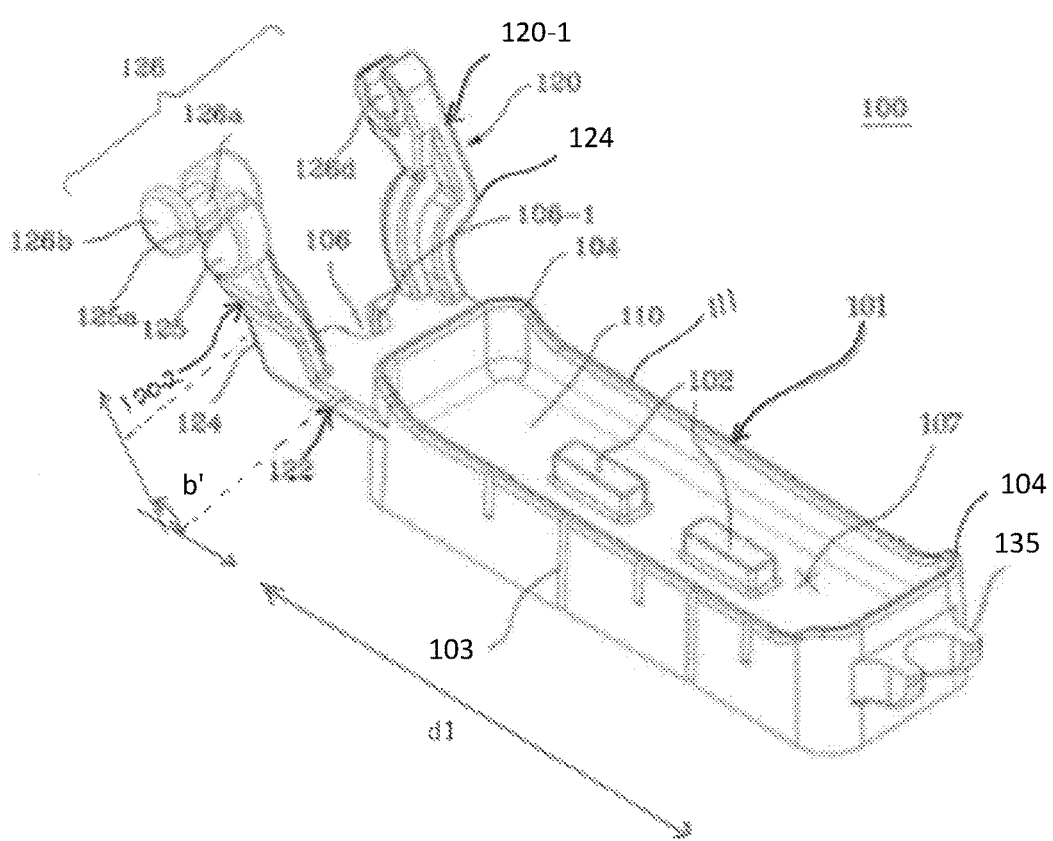
FIG. 2 is a diagram conceptually illustrating an example of an embodiment in accordance with an aspect of the present disclosure.
Figure 3:
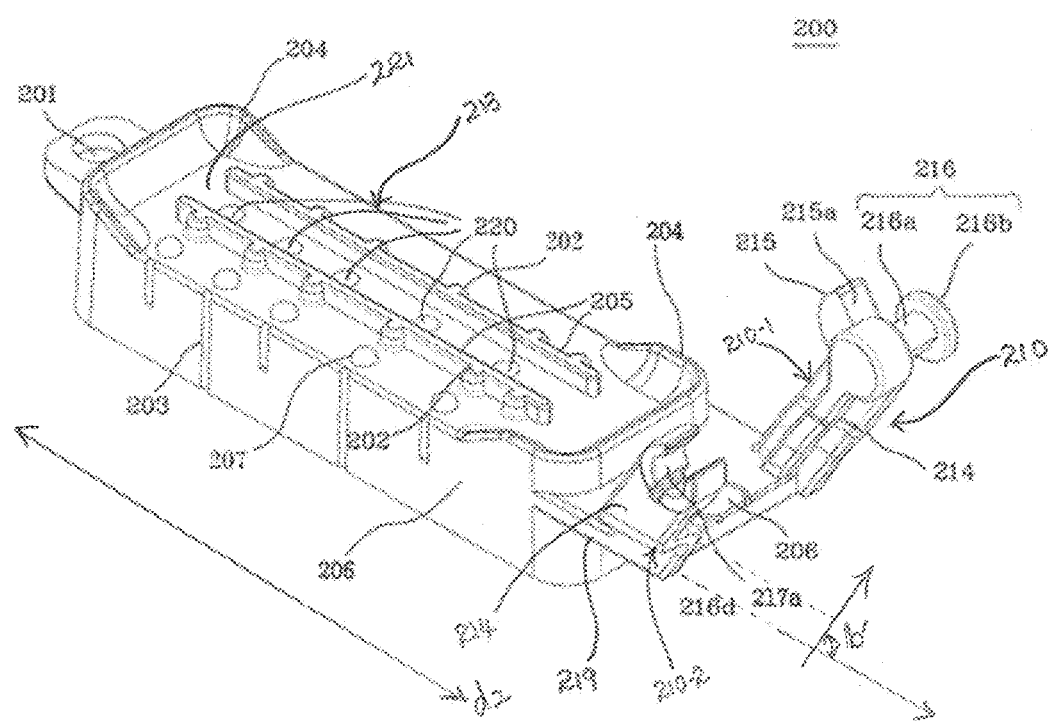
FIG. 3 is a diagram conceptually illustrating an example of an embodiment in accordance with an aspect of the present disclosure.

FIGS. 2 and 3 provide more detailed views of the first base 100 and the second base 200, respectively.

In the example shown in FIG. 2, the first base 100 may include various parts or components. By way of example, the first base 100 may include an elongated body 101 (or a first base body), a first extension portion 122 coupled to one end of the elongated body 101, and a first hinge portion 120 coupled to the first extension portion 122. The elongated body 101 may include a first groove 110 and enclosure (or side) walls 111 surrounding the first groove 110. The first groove 110 may be configured to include a space for receiving a material such as gypsum, plaster or the like. Also, the first groove 110 may be formed to correspond to the form of the elongated body 101 to match a shape of the elongated body 101.

In the example, the plaster (not shown) may be used to create a mold for making a crown. The plaster may include certain types of materials, such as metal, ceramic, plastic, or etc. Also, the plaster may be made from a mixture of water and gypsum powder. Typically, gypsum is a mineral used to make dental models or study casts in the form of dehydrate of calcium sulfate. In the example shown in FIG. 2, the gypsum or plaster may be injected or applied in the first groove 110 of the first base 100 in a longitudinal direction d1 of the elongated body 101.

In one implementation, the first extension portion 122 of the first base 100 may be coupled to the elongated body 101 of the first base 100 as an integral part of the first base 100 and coupled to the first hinge portion 120. Further, the first hinge portion 120 may include a pair of hinge portions 120-1 and 120-2 for the purpose of coupling the first base 100 to the second base 200 to form the articulator. Further, the first extension portion 122 which is coupled to the elongated body 101 of the first base 100 may extend from one longitudinal end of the first base 100 in the longitudinal direction d1. Further, in an aspect of the present disclosure, the first hinge portion 120 may be flexible enough to accommodate a relative rotation, a twist, or bending of the first hinge portion 120 without breaking. Furthermore, in another aspect of the present disclosure, the first extension portion 122 of the first base 100 may extend from one end of the elongated body in a longitudinal direction d1 and may form a predetermined angle b' with respect to the first hinge portion 120. For example, in one implementation, the predetermined angle b' may be about 75 degrees.

As noted, the first extension portion 122 may include the interlocking hole 106 which include one or more protrusions 106-1 inside the interlocking hole 106 as shown in FIG. 2. The one or more protrusions 106-1 may be configured to couple to the occlusion pin 500.

In an aspect of the present disclosure, the first groove 110 may include one or more protrusions 102 disposed on a bottom surface of the first groove 110 inside the elongated body 101 of the first base 100. Each of the protrusions 102 may be configured to protrude upward from the bottom surface of the first groove 110 and may be in various sizes and shapes. In the example, the protrusions 102 may be in, for example, a rectangular, a parallelepiped or a polygonal shape, and may not be necessarily limited to the sizes and shapes disclosed herein. Further, when the plaster 10 (shown in FIGS. 7 and 8) is placed or applied in the first groove 110 of the first base 100, the plaster 10 may be placed on or over the one or more protrusions 102 and then fix into a positive impression after hardening for a certain period of time. The positive impression provides a working model of a person's oral structure for manufacturing one or more crowns such that a dental technician may reliably operate.

Further, in an aspect of the present disclosure, the elongated body 101 of the first base 100 may include one or more additional structures, such as side walls 111 and overflow prevention walls 104 at one or more ends of the elongated body 101 of the first groove 110. The overflow prevention walls 104 may be configured to prevent any overflow of the plaster being placed in the first groove 110 of the first base 100. In the example, the overflow prevention walls 104 are disposed both ends of the elongated body 101 of the first base 100, but may not be limited to the present disclosure. The overflow prevention walls 104 may be disposed such a way that the overflow prevention walls 104 may significantly reduce unwanted plaster flows, thereby preventing any waste, as well as keeping the articulator and the working area clean, compared to the existing or conventional technology.

In another aspect of the present disclosure, the first base 100 may further include interlocking parts (or interchangeably referred to herein as "locking holes") 135 and 106 at the ends of the elongated body 101 of the first base 100. The interlocking parts 135 and 106 may be used to securely hold the first base 100 and the second base 200 via one or more occlusion pins 500 which are configured to be inserted in the interlocking parts 135 and 106.

In another aspect of the present disclosure, the first base 100 may further include one or more guide pin position markers 103 on one or more side walls 111 of the elongated body 101 of the first base 100. The one or more guide pin position markers 103 may be used to help locate or pin position of one or more guide pins inserted in the second base 200.

In an aspect of the present disclosure, as noted above, the first hinge portion 120 may include the pair of extension couplers 120-1 and 120-2 which extend upward from the first extension portion 122 with the predetermined angle b with respect to the first extension portion 122. The pair of extension couplers may include a left first extension coupler 120-2 and a right first extension coupler 120-1. The left first extension coupler 120-2 may include a first stopper 125 with a slanted portion 125a, a first coupler 126 which includes a first coupler pin 126a and a first coupler retaining plate 126b, and an extension body 124 coupled to the first stopper 125 and the first coupler 126. The first coupler retaining plate 126b may be in the form of a circular shape or may be in any other geometric shape.

Further, the first coupler pin 126a may be configured to couple to a second coupling groove 217a of the second hinge portion 210 of the second base 200 (as shown in FIG. 3), thereby coupling the first base 100 with the second base 200. The right first extension coupler 120-1 may include a first coupling groove 126d and an extension body 124 coupled to the first coupling groove 126d. The first coupling groove 126d may be configured to couple to a second coupler pin 216a of the second hinge portion 210 of the second base 200 (as shown in FIG. 3), thereby coupling the first base 100 with the second base 200. In other words, in the example, the first coupler pin 126a may be configured to engage with the second coupling groove 217a of the second base 200, by inserting or snapping the first coupler pin 126a into the second coupling groove 217a of the second hinge portion 210 of the second base 200. Also, the first coupling groove 126d may be configured to engage with the second coupler pin 216a of the second base 200, by receiving the second coupler pin 216a of the second base 200 into the first coupling groove 126d of the first base 100.

FIG. 3 provides a detailed view of an example of the second base 200. In an aspect of the present disclosure, the second base 200 may include an elongated body (or interchangeably referred herein as the second base body) 213, a second extension portion 219 coupled to the elongated body 213, and a second hinge portion 210 coupled to the second extension portion 219. The elongated body 213 of the second base 200 may include a second groove 221 and may correspond in size and shape to those of the first base 100.

The second base 200 may further include interlocking parts (or locking holes) 201 and 206, which are coupled to the side ends of the elongated body 213 of the second base 200. Further, the second extension portion 219 may extend in a longitudinal direction d2 from one end of the elongated body 213 of the second base 200 and may couple to the second hinge portion 210.

In an aspect of the present disclosure, the second hinge portion 210 may include a pair of extension couplers 210-1 and 210-2. That is, the second hinge portion 210 of the second base 200 may include a left second extension coupler 210-2 and a right second extension coupler 210-1, both of which are disposed on the second extension portion 219 of the second base 200. The left second extension coupler 210-2 and the right second extension coupler 210-1 each may be configured to extend upward from the second extension portion 219 at a predetermined angle b' with respect to the second extension portion 219.

Figure 4A:
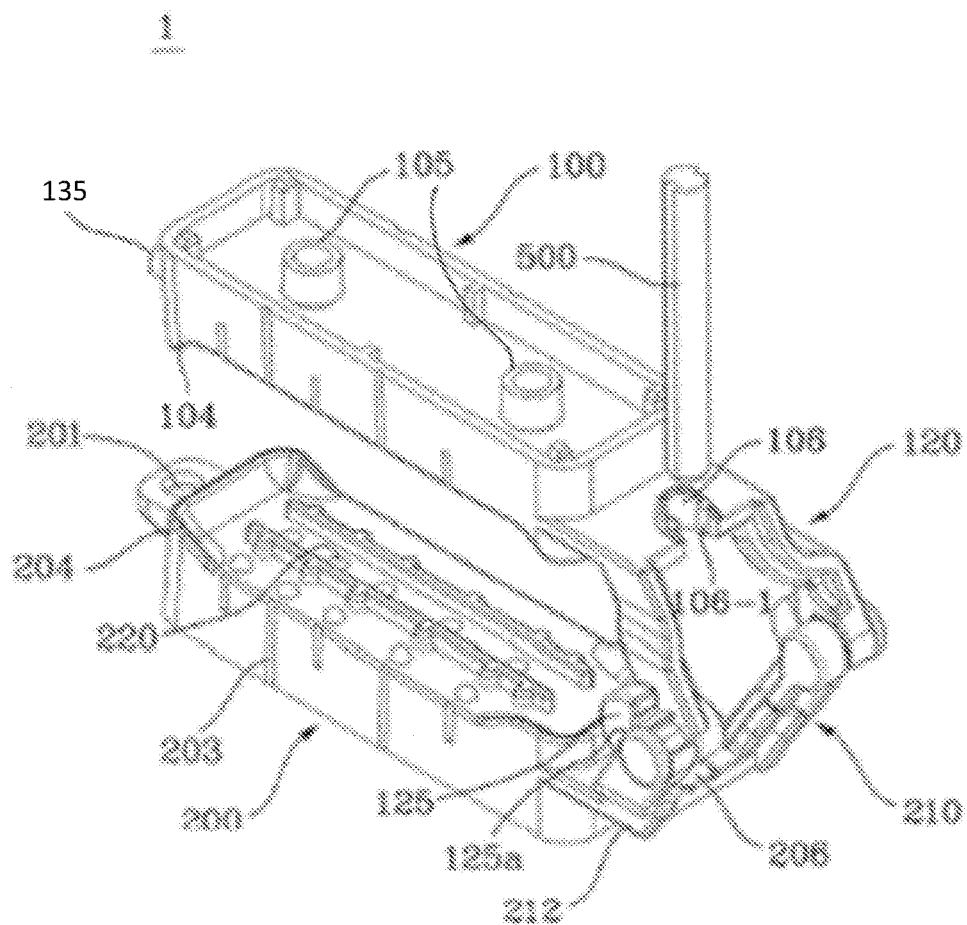
FIGS. 4A and 4B are diagrams conceptually illustrating an example of an embodiment in accordance with an aspect of the present disclosure.

The left second extension coupler 210-2 may include a second coupling groove 217a and an extension body 214 coupled to the second coupling groove 217a. The second coupling groove 217a may be further configured to engage with the first coupler pin 126a of the first base 100, as shown in FIG. 4A, for example. The right second extension coupler 210-1 may include a second coupler pin 216a, a second stopper 215 with a slanted portion 215a, a second coupler retaining plate 216b coupled to the second coupler pin 216a, and an extension body 214 coupled to the second stopper 215 and the second coupler pin 216a. The slanted portion 215a of the second stopper 215 may be configured to stop the engagement of the first hinge portion 120 of the first base 100.

In an aspect of the present disclosure, the second extension portion 219 may extend in the longitudinal direction d2 and may include an interlocking hole 206 disposed on a portion of the second extension portion 219 between the left second extension coupler 210-2 and the right second extension coupler 210-1.

In an aspect of the present disclosure, the second groove 221 of the second base 200 may include a plurality of pin holes 220, a plurality of extension protrusions 205 on a bottom surface of the second groove 221, one or more overflow prevention walls 204, and a side wall 206. The side wall 206 may include one or more guide pin position markers 203 on an outer surface of the side wall 206. Further, the plurality of extension protrusions 205 may include one or more support protrusions 202 disposed at one or both sides of the extension protrusions 205.

Further, in one implementation, the extended protrusions 205 may be spaced apart at a regular interval, facing each other relative to the pin holes 220 in a symmetrical pattern. In another aspect of the present disclosure, formation of the support protrusions 202 may be done to ensure cohesion of the plaster when the plaster is applied in the second groove 221 of the second base 200. Further, the support protrusions 202 may also be disposed at a predetermined interval, extending along the longitudinal direction d2 of the extended protrusion 205.

As noted above, the second base 200 may be configured to have a size and shape corresponding to those of the first base 100, and the second hinge portion 210 may be configured to engage with the first hinge portion 120. Further, as noted above, the first hinge portion 120 and the second hinge portion 210 may be flexible enough so that the second base 200 may be rotated or twisted via the second hinge portion 210, against the first base 100. Also, the first groove 110 of the first base 100 may be aligned with a center of a prosthetic abutment which is to be formed on a negative impression disposed on the plaster 10 which is applied on the first base 100. Another layer of plaster may be applied or placed on the negative impression disposed in the first base 100, and the second base 200 may be folded to be in the closed configuration for a molding or hardening process. After the molding process, the opposite may be formed. Also, in an aspect of the present disclosure, for accurate occlusion of the first base 100 and the second base 200, a pin may be inserted into one of the pin holes 220 to lead the rest of the one or more guide pins. Then, an occlusion pin 500 may be inserted into the interlocking parts of the first base 100 and the second base 200 for the tighter occlusion position.

Figure 4B:
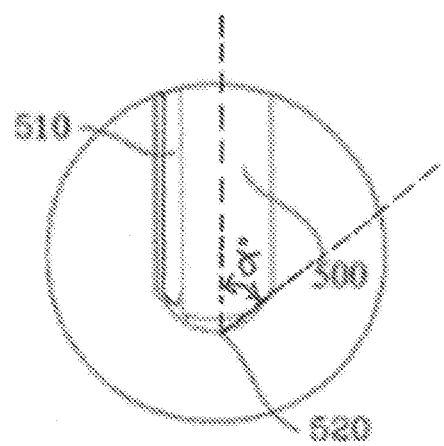

FIGS. 4A and 4B illustrate an example of an articulator in a closed configuration for occlusion operation. As shown in FIGS. 4A and 4B, the first base 100 and the second base 200 may be folded or closed via the coupling mechanism, e.g., the first hinge portion 120 and the second hinge portion 210. That is, the first base 100 may couple to the second base 200 by engaging the first base 100 with the second base 200, that is, by snapping the first coupler pin 126*a* of the first base 100 into the second coupling groove 217*a* of the second base 200, and by snapping the second coupler pin 216*a* of the second base 200 into the first coupling groove 126*d* of the first base 100, as shown in FIG. 4A. As such, the engagement of the first base 100 and the second base 200 result in forming the articulator.

The present technology described herein may provide many advantages over the existing or conventional technology in various aspects. In an aspect of the present disclosure, the technician may easily release and assemble the first base 100 and the second base 200 to form the articulator via the coupling mechanism.

Further, when the first base 100 and the second base 200 are folded up to form the articulator, each of the stoppers 215 and 125 may come in direct contact with the respective parts of the first extension couplers and the second extension couplers to stop the other part at a certain position and an angle. This may provide in turn more stability to the articulator when used.

Also, the occlusion pin 500 as shown in FIG. 4 may be used for engaging the first base 100 with the second base 200 for tighter coupling of the first base 100 and the second base 200 in the closed configuration as the articulator. In particular, the occlusion pin 500 may be inserted through the interlocking hole 106 of the first base 100 and the corresponding interlocking hole 206 of the second base 200.

In an aspect of the present disclosure, the occlusion pin 500 may include one or more guide channels or grooves 510 along an elongated body of the occlusion pin 500. Further, at one end of the elongated body of the occlusion pin 500, the occlusion pin 500 may include a protrusion extension point 520 for easier or smoother insertion into the interlocking holes 106 and 206, as well as for allowing a certain amount of lateral and horizontal movement during the use of the articulator by the operator or technician. In particular, in an aspect of the present disclosure, the protrusion extension point 520 may include a surface angle α of about 20 to 30 degrees with respect to a center line of the elongated body of the occlusion pin 500, as shown in FIG. 4B.

In an aspect of the present disclosure, a second occlusion pin (not shown) may be inserted into interlocking hole 135 of the first base 100 and the corresponding interlocking hole 201 of the second base 200. In the example, the interlocking hole 135 and/or the interlocking hole 106 of the first base 100 may be formed in a U-shape with an open end. Alternatively, the interlocking hole 135 and the interlocking hole 106 of the first base 100 may be in other shapes.

Also, as noted above, when plaster or gypsum may be applied and occlusion may be obtained by combining the first base 100 and the second base 200, the overflow prevention walls such as 104 and 204 may be used to minimize any overflow of the gypsum or plaster, thereby preventing any unnecessary waste. Further, the overflow prevention walls 104 and 204 may help to reduce contamination of a surrounding work area, and thus shorten a time needed for a general work process.

Further, in an aspect of the present disclosure, the first base 100 may include one or more protrusions 105 having pin holes therein disposed on an opposite side of the first groove 110 to facilitate removal of the plaster from the first groove 110. In one implementation, the one or more protrusions 105 having pin holes therein may project toward the outside in a cylindrical shape. In another implementation, the protrusion 105 having pin holes therein may be designed for other shapes and/or replacement.

After the plaster is applied and hardened (or the gypsum has coagulated) in the first groove 110 of the first base 100, the one or more protrusions 105 having pin holes therein may be hit or provided with a few solid taps with a small hammer or a mallet or a similar tool, to provide impact for separating the plaster from the first base 100. In the example, the gypsum may absorb the impact and be easily removed from the first groove 110 of the first base 100. Thus, the technician may separate the gypsum without any difficulty, thereby improving the speed and workability during the manufacturing process.

Figure 5:
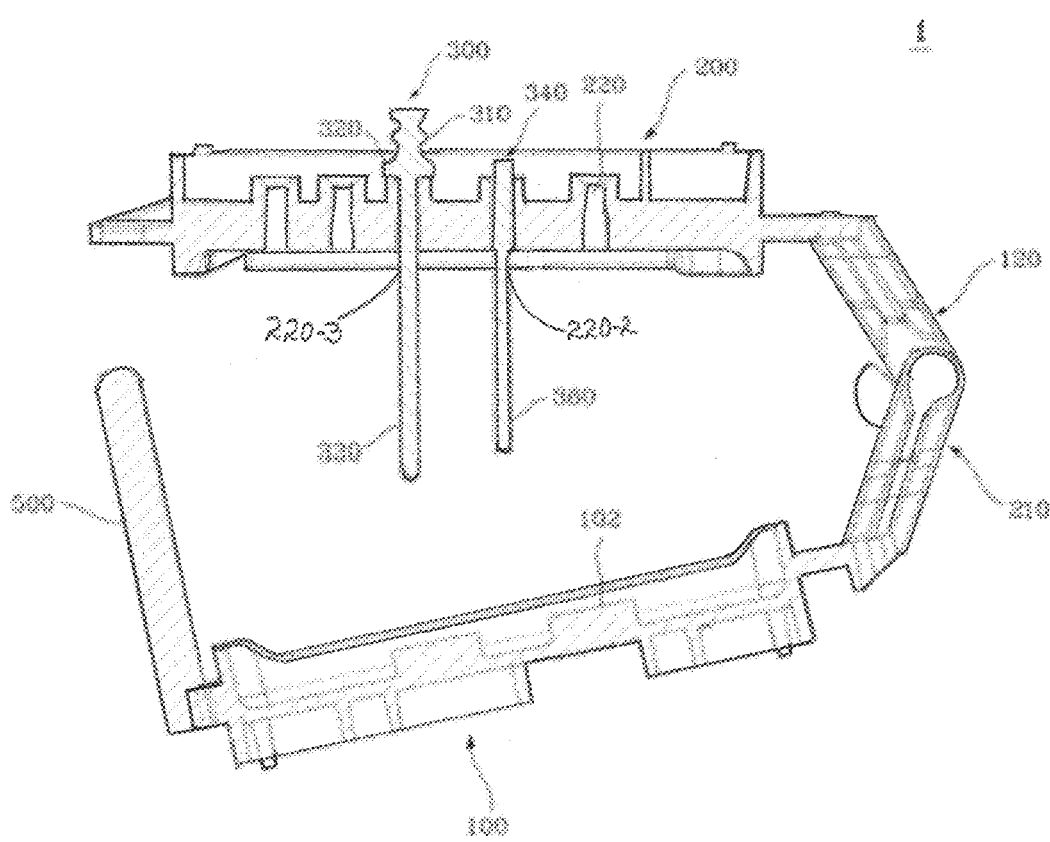
FIG. 5 is a view illustrating an example of an embodiment of a position pin inserted into an example of an articulator in an aspect of the present disclosure.

FIG. 5 is an example of a side cross-sectional view in accordance with an aspect of the present disclosure. In the example shown in FIG. 5, multiple position pins 300 and 340 are inserted in the second base 200. By way of example, a first position pin 300 may be inserted into a pin hole 220-3 of the second base 200. The first position pin 300 may include a handle 310, an interlocking portion 320, and an elongated pin body 330 coupled to the handle 310 and the interlocking portion 320.

As shown in FIG. 5, when the first position pin 300 is inserted into the pin hole 220-3 of the second base 200, the elongated pin body 330 may extend below the second base 200 towards the first base 100. Also, shown is a second position pin 340 including a pin body 360 which is inserted into the pin hole 220-2 and extends below the second base 200 towards the first base 100. Although the example shown in FIG. 5 includes the first position pin 300 and the second position pin 340, it may not be limited thereto, and as such, additional position pins may be inserted in multiple pin holes of the second base 200.

Figure 8:
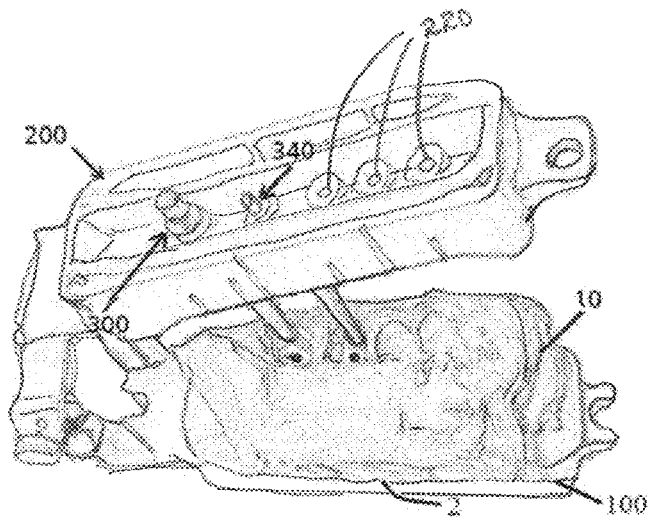

In one implementation, the first position pin 300 may have a non-uniform weight distribution throughout the first position pin 300. That is, the elongated pin body 330 of the first position pin 300 may be designed to have a greater weight than that of the interlocking portion 320 of the first position pin 300. Further, the interlocking portion 320 of the first position pin 300 may include a larger body or a larger diameter than that of the pin body 330. These attributes of the first position pin 300 may result in that the first position pin 300 may be positioned at a center of a target abutment's upper surface (not shown) and maybe used to accurately mark or indicate a location of a center of the target abutment (as shown in FIG. 8). That is, because the pin body 330 of the first position pin 300 may be heavier in weight than the weight of the handle 310 and the interlocking portion 320, the first position pin 300 may be easily dropped and inserted into the pin hole 220 (or 220-3) by means of gravity. When the first position pin 300 is inserted into the pin hole 220-3, a lower end of the pin body 330 may be positioned or dropped at the center of the prosthetic target abutment 3. As a result, the first position pin 300 and/or the second position pin 340 may help the technician to accurately determine the center of the prosthetic target abutment 3 and perform subsequent operations with ease.

In another aspect of the present disclosure, the first position pin 300 may include irregularities (e.g., tapering or irregularities) on the handle 310 of the first position pin 300 such that the technician may securely hold and manipulate the first position pin 300 into the pin holes 220-3 of the second base 200.

Further, the technician may insert the first position pin 300 into a target abutment 3 disposed in the first base 100, through the pin hole 220 on the second base 200 without running into any problems. Also, in an aspect of the present disclosure, the second base 200 may be designed in such a way that the second base 200 may be easily rotated or twisted by means of the second hinge portion 210 which couples with the first hinge portion 120 of the first base 100.

Referring back to FIG. 5, the second position pin 340 may be inserted into the pin hole 220-2. In another implementation, the second position pin 340 may include an upper portion and a lower portion of a pin body 360 which extends through the pin hole 220-2. The lower portion of the pin body 360 may have a constant diameter and extend in an elongation direction to a predetermined length.

Also, as described above, the second position pin 340 may have features similar to those of the first position pin 300. In an aspect of the present disclosure, by disposing the lower portion of the pin body 360 at the center of the target abutment 3, the occlusion may be determined more accurately.

From an operational perspective, after determining the center of the target abutment 3, the technician may then apply gypsum onto the first groove 110 of the first base 100. After applying the gypsum, the technician may place a dental impression 2 on a lower face of the plaster. When the plaster is applied to the dental impression 2 placed on the first groove 110 of the first base 100, the second base 200 may be rotated or folded to face the first base 100 via the second hinge portion 210 that is coupled to the first hinge portion 110.

In an aspect of the present disclosure, the dental impression 2 may be disposed on an upper surface of the first base 100 facing the second base 200. The first position pin 300 may then be inserted into the second base 200. The pin body 330 of the first position pin 300 may then be adjusted to the ends of the prosthetic abutment target 3 towards a center position by inserting the first position pin 300 into one of the pin holes 220 of the second base 200.

As noted above, along a side edge of the second base 200, the second base 200 may include overflow prevention walls 204 for preventing an overflow of plaster or gypsum, disposed on a front end and a rear end relative to a longitudinal direction extending toward an upper side, as shown in FIG. 4.

Figure 9:
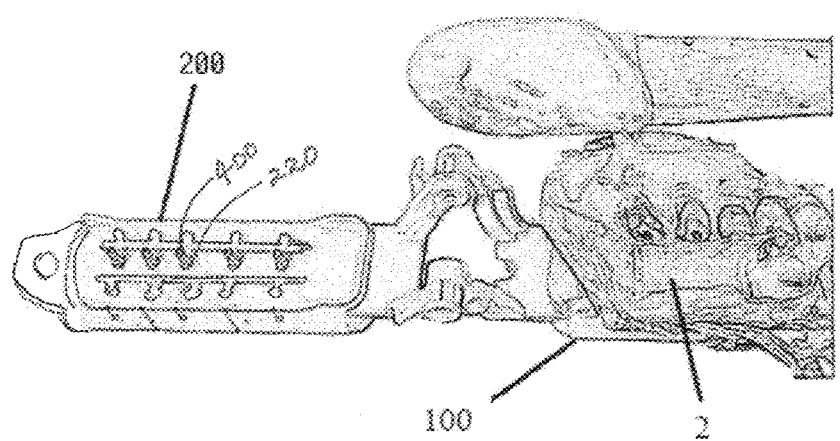

Further, in another aspect, one or more guide pins 400 may be inserted respectively in the pin holes 220 of the second base 200, as shown in FIG. 1. Also, the one or more guide pins may protrude more than a predetermined length toward an upper portion of the pin hole 220 (as shown in FIG. 9).

Referring back to FIG. 3, in an aspect of the present disclosure, the support protrusions 202 may be configured to ensure cohesion of the plaster when the plaster is applied. Further, as noted above, the multiple support protrusions 202 may be disposed at predetermined intervals, extending along the longitudinal direction d2 of the extended protrusion 205. When separating the prosthetic abutment from other abutments that are manufactured, the support protrusions 202 may help to prevent any axial rotation of the guide pins inserted in the pin holes 220 after the plaster has been injected or placed. As such, it may be possible to minimize the left, right, up, down movements needed to achieve a stable operation of the articulator to practice a precise prosthetic work.

Further, the multiple support protrusions 202 may be disposed symmetrically on the left and right sides of the pin holes 220. The one or more guide pins may be used to maintain the stability of the prosthetic target abutment 3 or the surrounding teeth. When the technician uses a jigsaw 11 (shown in FIG. 12) or a similar tool to separate the prosthetic abutment 3 (or the target abutment) or other teeth from the surrounding area, the target abutment 3 may be precisely cut off, because of use of the one or more guide pins, thereby improving the operation.

Figure 6:
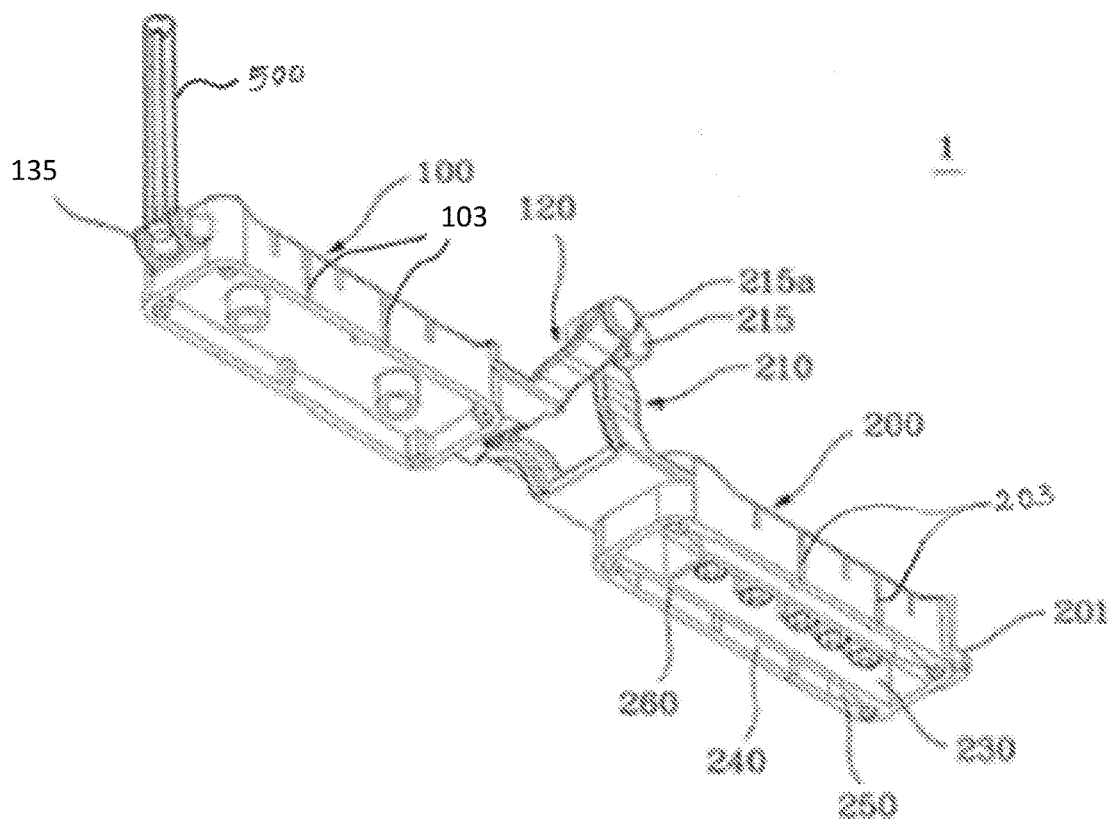
FIG. 6 is another perspective view conceptually illustrating the example of the articulator in an open position in accordance with an aspect of the present disclosure.

FIG. 6 illustrates an example of the articulator in an open configuration. By way of example, the first base 100 and the second base 200 are coupled to each other via the first hinge portion 120 and the second hinge portion 210. Further, in the example, the occlusion pin 500 is shown as being disposed in the interlocking hole 135. Also, in an aspect of the present disclosure, the second base 200 may include a partition wall 230 for partitioning an inside region of a bottom portion of the second base 200 in a longitudinal direction relative to the one or more pin holes 220. The partition wall 230 may be formed to inject or apply the plaster or gypsum. Further, the second base 200 may further include an inner space or a second groove 240, which is formed by the partition wall 230 and walls of the second base 200, into which the plaster may be applied.

The second base 200 and the second hinge portion 210 may face away from each other on a surface which includes the occlusion pin 500. The occlusion pin 500 may be inserted into an interlocking hole 201 of the second base 200. Also, the interlocking hole 135 of the first base 100 may be formed in a lower side of the overflow prevention wall 104 as a U-shape to receive the occlusion pin 500 inserted therein.

The interlocking hole 135 or 201 may further provide guidance for the reliable entry of the occlusion pin 500. Further, when the occlusion pin 500 is inserted into the interlocking hole 135 or 201, the accuracy of operation may be improved by providing more tight coupling of the first base 100 and the second base 200. As such, the lateral as well as horizontal movements may be controlled. Further, the occlusion pin 500 may be designed in such a way that a predetermined amount of lateral and horizontal movements of the first base 100 or the second base 200 may be possible via a protrusion extension point disposed at one end of the elongated body of the occlusion pin 500. For example, as noted above, the protrusion extension point at the one end of the occlusion pin 500 may have an angle of about 20 to 30 degrees with respect to a center line of the elongated body of the occlusion pin 500.

In an aspect of the present disclosure, a hole 206 may be provided to guide correct occlusion by preventing an excessive lowering of a bottom of the occlusion pin 500.

In another aspect of the present disclosure, the guide pin position may allow the pin holes 220 on the second base 200 to be used wherever on the surface, whether it be a front surface or a back surface and according to a positive and negative angles of the pin. As a result, the technician may visually recognize the pin position in an accurate manner.

In an aspect of the present disclosure, in FIG. 6, the second groove 240 may be formed in such a way that a volume of the second groove 240 may gradually decrease from opposite left and right positions, relative to a longitudinal direction of a volume reduction unit 250, which may prevent any deformation of the second base 200 as the volume of the gypsum expands. The volume reduction unit 250 may be configured to reduce any issues arising from the injection of the plaster into the space provided for preventing any deformation of the second base 200 as the volume of the plaster expands.

Further, in the example, the second base 200 may include a sticky adhesive portion 260 at a bottom of the partition wall 230 to provide an adhesive surface to a belt in the form of stickers (not shown). The sticky adhesive portion 260 may prevent the plaster from being further injected into the inner zone, and thus it may be possible to prevent any twisting, bending, and/or deformation due to an influx of the gypsum. As such, the accuracy and convenience of the prosthetic work by the technician may be greatly improved.

When the technician obtains the prosthetic target abutment 3 as disposed in the second base 200 and the first base 100, a front or rear surface of the second base 200 may include one or more markings to determine a cutting position. For example, the second base 200 or the first base 100 may each include one or more guide pin position markers 203 on the side wall that is placed at a position, may correspond to the location of the one or more guide pins inserted into the pin holes 220 in a longitudinal direction of the front and rear surfaces.

Having discussed various aspects of the articulator, the following description provides example users of the articulator in various aspects of the present disclosure. FIGS. 7-15 illustrates example uses of the articulator described herein in accordance with various aspects of the present disclosure.

Figure 7:
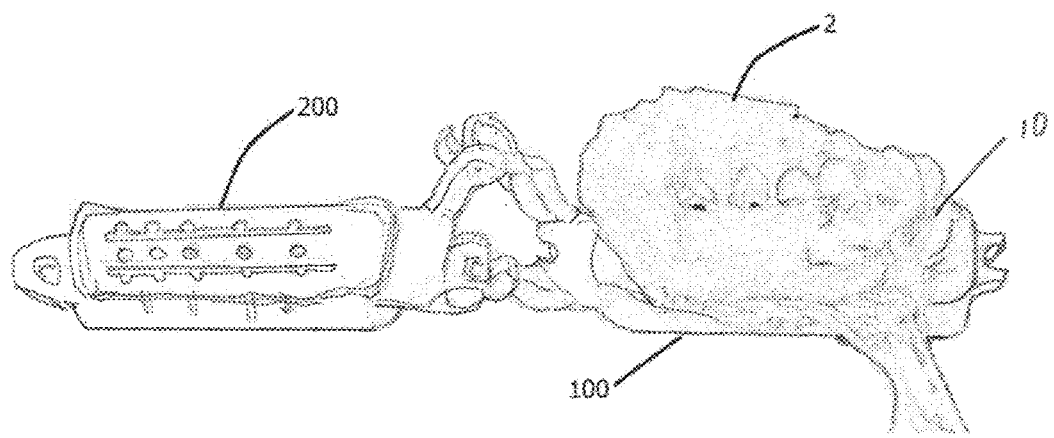
FIGS. 7-15 are various views conceptually illustrating various views of example uses of the articulator in accordance with aspects of the present disclosure.

FIG. 7 shows a plaster 10 (or die stone) disposed or poured into the first base 100 of the articulator and a dental impression 2 (or an impression) placed on top of the plaster 10. The articulator is in an open configuration. The dental impression 2 is a negative imprint of hard teeth and soft tissues in the mouth from which a positive reproduction or cast may be formed using the plaster or gypsum. Typically, the dental impressions are made by using a container designed to fit over the dental arches or trays. Liquid or semi-solid impression materials are mixed and placed or dispensed in a dental impression tray, and placed into the mouth, and then set or harden to a solid, leaving an imprint of the structures in the mouth of a person. The dental impression obtained in such a way provides a negative of teeth, capturing a part or all of a person's development and arrangement of teeth and surrounding structures of oral cavity.

FIG. 8 shows an example of the articulator in a semi-closed position with multiple position pins. In the example, position pins 300 and 340 are inserted into the pin holes 220 of the second base 200 to align centers on the dental impression 2. The black dots on the dental impression indicate the centers of the target abutment.

In FIG. 9, the articulator is in the open configuration and the plaster is applied on the dental impression 2. Also, in the example, a plurality of position pins 400 is inserted in the pin holes 220 of the second base 200. In FIG. 9, the plaster (or die stone or stone mixture) is applied over the plurality of position pins 400 on the second base 200 and/or over the dental impression 2 to obtain a dental cast (or the positive impression) or an abutment target.

Figure 10:
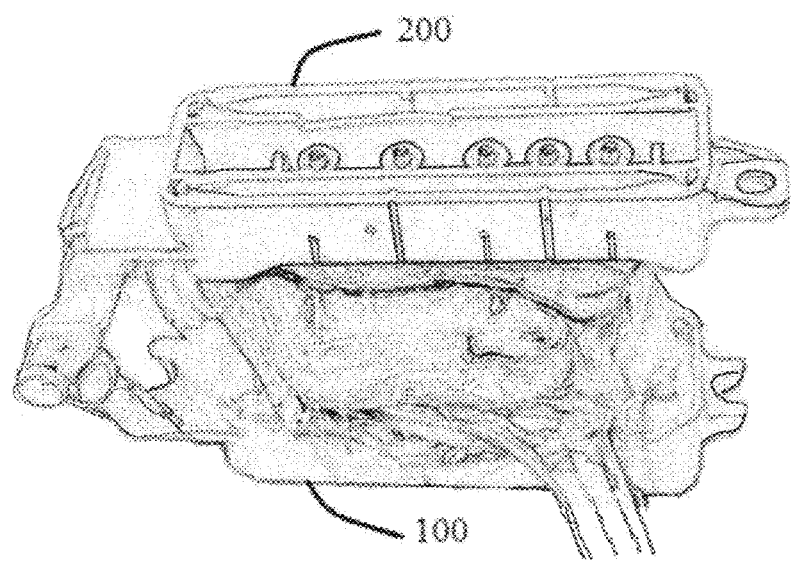
Figure 11:
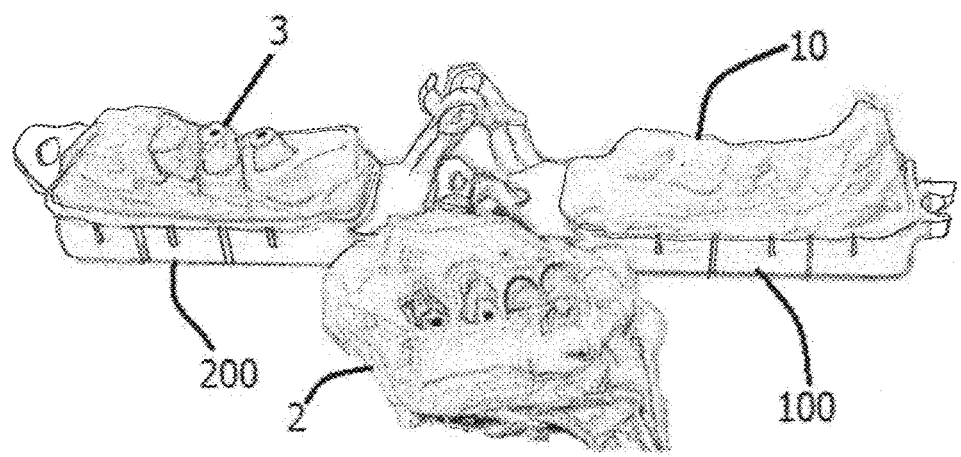

As shown in FIG. 10, after the plaster is applied on the dental impression 2 as shown in FIG. 9, the articulator is folded to be in the closed configuration and allowed to sit for a predetermined period of time. That is, the second base 200 is folded or rotated toward the fist base 100 with the dental impression 2 and the plaster applied there between. The articulator is to remain in an occlusion position for a certain period of time, e.g., 45 minutes, for a hardening process. The occlusion pins may be used for tighter coupling the first base 100 and the second base 200. After the passage of the predetermined amount of time, the articulator may be opened, i.e., the second base 200 and the first base 100 may be in an open configuration, as shown in FIG. 11, and the dental impression may be removed from the articulator, thereby leaving the position impressions on the first base 100 and the second base 200.

Figure 12:
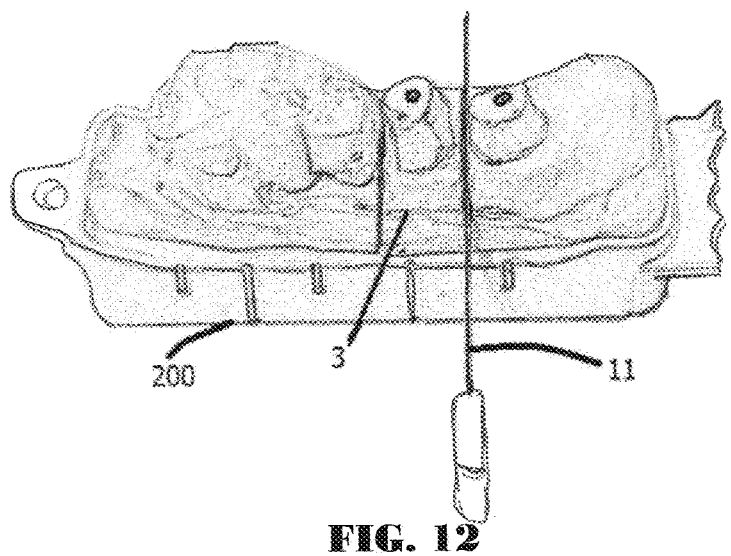

In the example, the dental impression 2 may be removed from the articulator and as shown in FIG. 12 one or more target abutments 3 may be obtained by cutting into individual pieces or working dies using a jigsaw 11. Each of the target abutments 3 may be an abutment which is a connecting element between the implant to a final outer crown. An abutment is sometimes called as an implant abutment or a prosthetic abutment. At this stage, the target abutment is obtained or made to custom fit a person's mouth corresponding to the dental impression 2.

Figure 13:
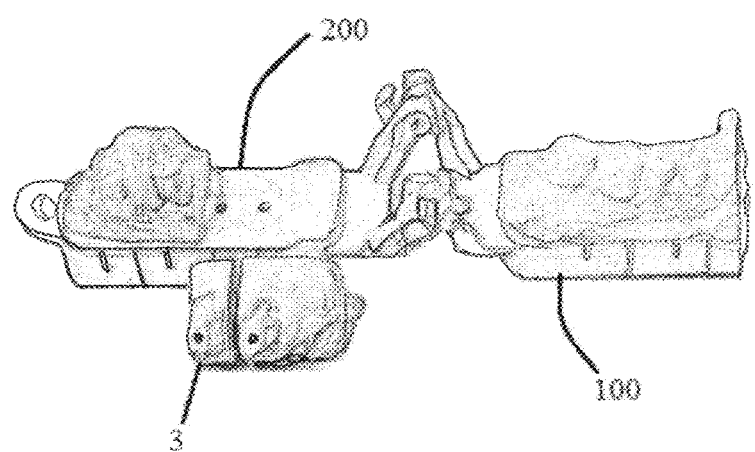
Figure 14:
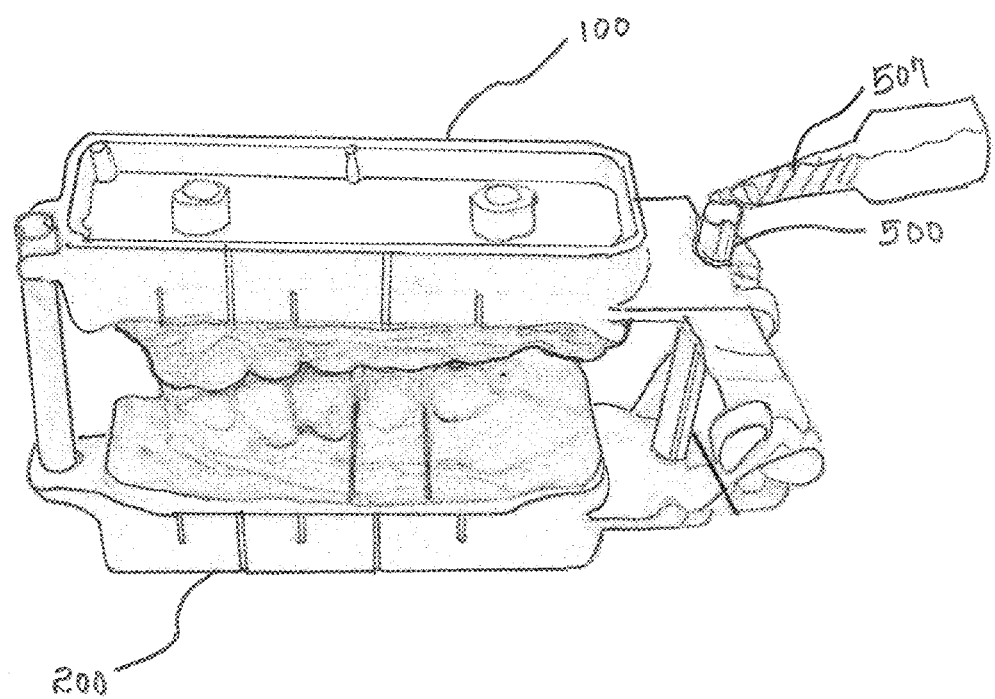
Figure 15:
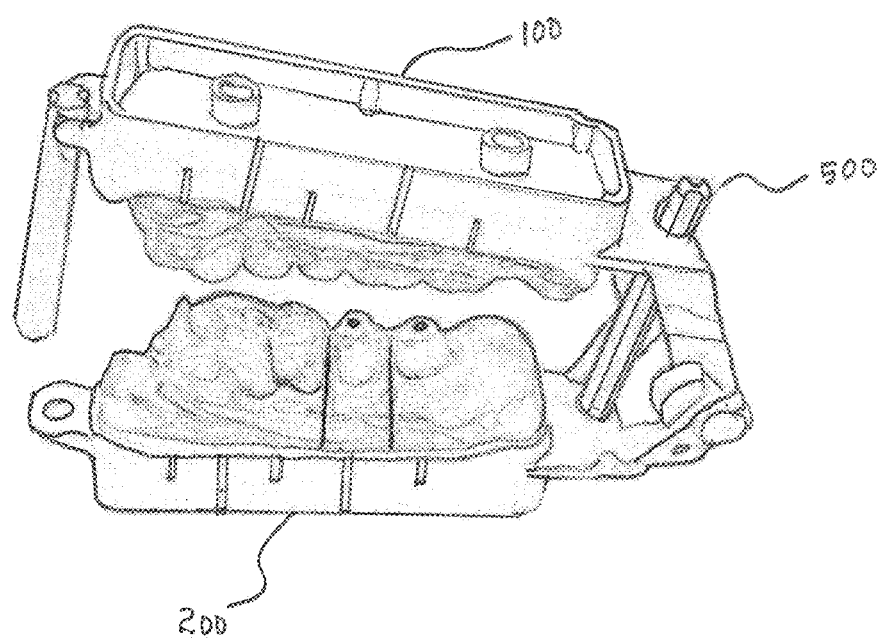

After obtaining the one or more target abutments 3 ("working dies") as shown in FIGS. 12 and 13, the articulator is closed again using the one or more occlusion pins 500 as shown in FIGS. 14 and 15. Further, as shown in FIG. 14, a glue 507 may be applied to a top portion of the occlusion pin 500 to help to securely hold and maintain a certain clearance between the second base 200 and the first base 100 in the articulator. Securing the occlusion pin 500 in such a manner helps to reduce errors in obtaining a precise clearance in a working model. FIG. 15 shows a slightly open position of the articulator after the glue 507 has been applied to the occlusion pin 500. The technician may rotate or twist the second base 200 for different working tasks. This helps to maintain the articulator in a stable condition for work that requires precision and accuracy. As such, the present disclosure provides improved technology including an improved articulator that will enable manufacture of a dental restoration in a more convenient, faster, and accurate manner, facilitating and improving work flows at a dental laboratory.

While for the purpose of simplicity the methodologies are described herein as a series of steps or acts, it is to be understood that the claimed subject matter is not limited by the order of steps or acts, as some steps or acts may occur in different orders and/or concurrently with other acts from that shown and described herein. Further, not all illustrated steps or acts may be required to implement various methodologies according to the present technology disclosed herein. Furthermore, the methodologies disclosed herein and throughout this specification are capable of being stored on an article of manufacture to facilitate transporting and transferring such methodologies to one or more processing systems. The term "article of manufacture" is intended to encompass a computer program accessible from any computer-readable device, carrier, or medium. A singular form may include a plural form if there is no clearly opposite meaning in the context. Also, as used herein, the article "a" is intended to include one or more items. Further, no element, act, step, or instruction used in the present disclosure should be construed as critical or essential to the present disclosure unless explicitly described as such in the present disclosure. As used herein, except explicitly noted otherwise, the term "comprise" and variations of the term, such as "comprising," "comprises," and "comprised" are not intended to exclude other additives, components, integers or steps. The terms "first," "second," and so forth used herein may be used to describe various components, but the components are not limited by the above terms. The above terms are used only to discriminate one component from other components, without departing from the scope of the present disclosure. Also, the term "and/or" as used herein includes a combination of a plurality of associated items or any item of the plurality of associated items. Further, it is noted that when it is described that an element is "coupled" or "connected" to another element, the element may be directly coupled or directly connected to the other element, or the element may be coupled or connected to the other element through a third element. A singular form may include a plural form if there is no clearly opposite meaning in the context. In the present disclosure, the term "include" or "have" as used herein indicates that a feature, an operation, a component, a step, a number, a part or any combination thereof described herein is present. Further, the term "include" or "have" does not exclude a possibility of presence or addition of one or more other features, operations, components, steps, numbers, parts or combinations. Furthermore, the article "a" as used herein is intended to include one or more items. Moreover, no element, act, step, or instructions used in the present disclosure should be construed as critical or essential to the present disclosure unless explicitly described as such in the present disclosure.

Although the present technology has been illustrated with specific examples described herein for purposes of describing example embodiments, it is appreciated by one skilled in the relevant art that a wide variety of alternate and/or equivalent implementations may be substituted for the specific examples shown and described without departing from the scope of the present disclosure. As such, the present disclosure is intended to cover any adaptations or variations of the examples and/or embodiments shown and described herein, without departing from the spirit and the technical scope of the present disclosure.

What is claimed is:

1. An articulator, comprising:
   a first base including:
      a first base body comprising a first inwardly facing groove configured to receive gypsum or plaster,
      a first hinge portion coupled to the first base body and configured to extend outwardly from one end of the first base body and
      a plurality of pin holes disposed in an outwardly facing groove of the first base body;
   a second base including:
      a second base body comprising a second groove configured to receive the gypsum or plaster,
      a second hinge portion coupled to the second base body and configured to extend outwardly from one end of the second base body, and
      a plurality of guide pin holes disposed in the second groove of the second base body, the second hinge portion being configured to couple to the first hinge portion of the first base; and
   an occlusion pin configured to couple the first base and the second base in a closed position, wherein the first base or the second base further comprises one or more guide pin markers on a side wall of the first base body or the second base body.

2. The articulator according to claim 1,
   wherein the first hinge portion of the first base comprises a pair of extension couplers disposed on a first extension part coupled to one end of the first base body, the pair of extension couplers of the first hinge portion including a left first extension coupler and a right first extension coupler;
   wherein the second hinge portion of the second base comprises a pair of extension couplers disposed on a second extension part coupled to one end of the second base body, the pair of extension couplers of the second hinge portion including a left second extension coupler and a right second extension coupler; and
   wherein the left first extension coupler of the first hinge portion is configured to couple to the left second extension coupler of the second hinge portion, and the right first extension coupler of the first hinge portion is configured to couple to the right second extension coupler of the second hinge portion.

3. The articulator according claim 2, wherein the left first extension coupler of the first hinge portion comprises a first stopper, a first coupler, and an extension body, and the right first extension coupler of the first hinge portion comprises a first coupling groove and an extension body; and
   wherein the left second extension coupler of the second hinge portion comprises a second coupling groove and an extension body, and the right second extension coupler of the second hinge portion comprises a second stopper, a second coupler, and an extension body.

4. The articulator according to claim 1, wherein the first groove of the first base further comprises a plurality of protrusions on a bottom surface of the first groove.

5. The articulator according to claim 1, wherein the first base further comprises a plurality of overflow prevention walls surrounding the first groove to prevent overflows of the gypsum or plaster that is applied.

6. The articulator according to claim 1, wherein the first base further comprises a plurality of interlocking parts each configured to receive the occlusion pin.

7. The articulator according to claim 6, wherein the second base further comprises a plurality of interlocking parts each configured to receive the occlusion pin, and the plurality of interlocking parts of the second base each corresponds to the plurality of interlocking parts of the first base.

8. The articulator according to claim 1, wherein the second groove of the second base further comprises a plurality of guide pin holes configured to receive a plurality of guide pins.

9. The articulator according to claim 1, wherein the second base further comprises a plurality of overflow prevention walls surrounding the second groove to prevent overflows of the gypsum or plaster.

10. The articulator according to claim 1, wherein the second groove of the second base includes a plurality of protrusions disposed on a bottom surface of the second groove and configured to ensure cohesion of the gypsum or plaster when the gypsum or plaster is applied.

11. The articulator according to claim 10, wherein the plurality of protrusions are disposed on the bottom surface of the second groove in a symmetric pattern around the plurality of guide pin holes.

12. The articulator according to claim 1, wherein the occlusion pin comprises an elongated body and a protrusion extension point at one end of the elongated body, the protrusion extension point having an angle with respect to a center line of the elongated body.

13. The articulator according to claim 12, wherein the protrusion extension point of the occlusion pin includes a predetermined angle of about 20 to 30 degrees with respect to the elongated body.

14. The articulator according to claim 1, wherein the occlusion pin includes one or more occlusion guide channels disposed in a longitudinal direction along an elongated body of the occlusion pin, and the one or more occlusion guide channels are configured to couple the occlusion pin to interlocking parts of the first base or the second base.

\* \* \* \* \*